United States Patent [19]

Aloup et al.

[11] Patent Number: 4,680,303

[45] Date of Patent: Jul. 14, 1987

[54] THIOFORMAMIDE DERIVATIVES AND USE IN INHIBITING GASTRIC SECRETION

[75] Inventors: Jean C. Aloup, Villeneuve-le-Roi; Jean Bouchaudon, Morsang-sur-Orge; Daniel Farge, Thiais; Claude James, Paris, all of France

[73] Assignee: Rhone-Poulenc Sante, Courbevoie, France

[21] Appl. No.: 798,846

[22] Filed: Nov. 18, 1985

[30] Foreign Application Priority Data

Nov. 20, 1984 [FR] France .................................. 8417648

[51] Int. Cl.$^4$ ................. C07D 409/00; C07D 401/00; A61K 31/44
[52] U.S. Cl. .................................... 514/336; 546/280; 546/268; 514/342
[58] Field of Search ............... 546/280, 268; 514/342, 514/336

[56] References Cited

U.S. PATENT DOCUMENTS 4,379,154  4/1983  Aloup et al. .................... 546/268

FOREIGN PATENT DOCUMENTS 0046417  2/1982  European Pat. Off. ............ 546/280
0073704  3/1983  European Pat. Off. ............ 546/280
0097584  1/1984  European Pat. Off. ............ 546/280
2046265  11/1980  United Kingdom ............... 546/280

Primary Examiner—Alan L. Rotman
Assistant Examiner—Robert C. Whittenbaugh
Attorney, Agent, or Firm—Stevens, Davis, Miller & Mosher

[57] ABSTRACT

Thioformamide derivatives of formula:

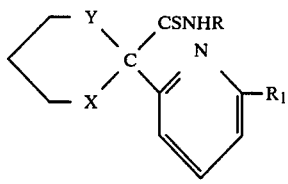

in which R is hydrogen or alkyl (1 to 4 C), $R_1$ is alkyl (1 to 4 C), and X denotes sulphur or oxygen and Y is sulphur, oxygen, methylene radical, or, when X is oxygen, a valency bond, are inhibitors of gastric secretion and therefore useful in the treatment of gastric ulcers. They may be made by reaction of an amine $R-NH_2$ with a corresponding thioester or, when R is alkyl, by reaction of an alkyl isothiocyanate with the product of reacting a base with a compound of formula:

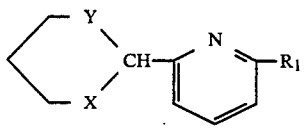

3 Claims, No Drawings

THIOFORMAMIDE DERIVATIVES AND USE IN INHIBITING GASTRIC SECRETION

The present invention relates to thioformamide derivatives useful in therapy and to their preparation and use.

The invention provides novel thioformamide derivatives of the formula:

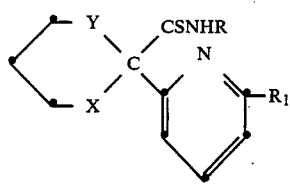
(I)

in which R denotes a hydrogen atom or a straight-chain or branched alkyl radical of 1 to 4 carbon atoms, $R_1$ denotes a straight-chain or branched alkyl radical of 1 to 4 carbon atoms, and either X denotes sulphur or oxygen and Y denotes sulphur, oxygen or methylene, or X denotes oxygen and Y denotes a valency bond. These compounds are useful in therapy as inhibitors of gastric secretion.

According to the feature of the invention, the compounds of formula (I) in which R, $R_1$, X and Y are as defined above are prepared by the reaction of an amine of the formula:

R-NH$_2$ (II)

in which R is as defined above, with a dithioester of the formula:

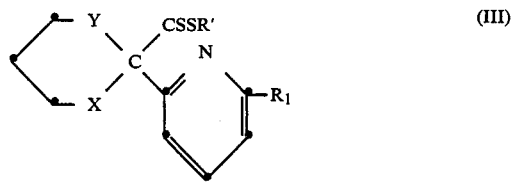
(III)

in which $R_1$, X and Y are as defined above, and R' denotes a straight-chain or branched alkyl radical of 1 to 4 carbon atoms or a benzyl or carboxymethyl radical.

In general, this reaction is performed with an excess of amine of formula (II), without a solvent or in an organic solvent such as an aromatic hydrocarbon, an ether or a low molecular weight alcohol, or a mixture of these solvents, at a temperature between 20° and 130° C., optionally under pressure.

The dithioesters of formula (III) can be obtained by the action of an organolithium derivative on a compound of formula:

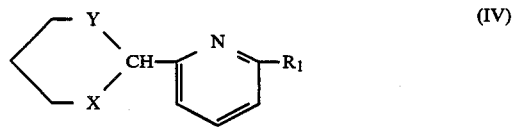
(IV)

in which $R_1$, X and Y are as defined above, followed by reaction of the product with carbon disulphide and then with a compound of formula:

R'-Z (V)

in which R' is as defined above and Z denotes a halogen atom, preferably a chlorine, bromine or iodine atom, or a reactive ester residue, preferably a mesyloxy or tosyloxy residue.

The reaction is generally performed in an anhydrous organic solvent such as hexamethylphosphorotriamide, to which an ether such as tetrahydrofuran is generally added, at a temperature between −80° and −40° C.

The organolithium derivative used is preferably a lithium alkyl, such as butyllithium or isopropyllithium, or phenyllithium, in solution in an inert solvent such as hexane, or a lithium amide such as lithium diisopropylamide or lithium isopropylamide.

According to the definitions of X and Y, the compounds of formula (IV) can be prepared by methods similar to those described or mentioned in European Patent Application No 0,046,417; thus:

(a) The compounds of formula (IV) in which $R_1$ is as defined above, X denotes sulphur, and Y denotes methylene, i.e. the compounds of formula:

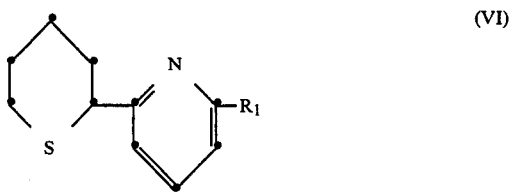
(VI)

can be prepared by cyclisation, using an organic base, of a compound of formula:

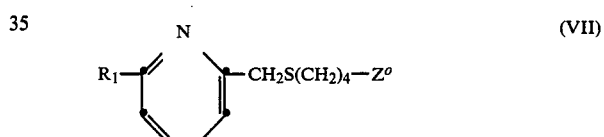
(VII)

in which $R_1$ is as defined above and Z' denotes a halogen atom, preferably chlorine or bromine, or a reactive ester residue, preferably a mesyloxy or tosyloxy residue, working in an anhydrous organic solvent such as tetrahydrofuran or hexamethylphosphorotriamide or a mixture of these solvents, at a temperature between −80° and +25° C. The organic base is preferably potassium tert-butylate, lithium diethylamide, lithium diisopropylamide or butyllithium.

The heterocyclic compounds of formula (VII) can be obtained by alkaline hydrolysis, preferably using an aqueous solution of an alkali metal hydroxide such as sodium hydroxide, of a salt of an isothiourea of formula:

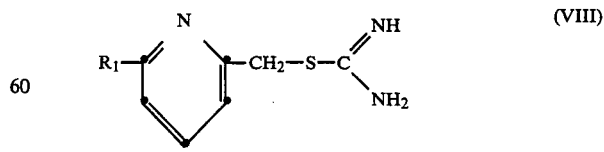
(VIII)

at a temperature between 50° C. and the boiling point of the reaction mixture, followed by the action of a compound of formula:

Z'-(CH$_2$)$_4$-Z' (IX)

in which the symbols Z', which may be identical or different, each denote a halogen atom, preferably a chlorine or bromine atom, or a reactive ester residue, preferably a mesyloxy or tosyloxy residue, at a temperature in the region of 20° C. in the presence of an alkali metal hydroxide such as sodium hydroxide.

It is possible to isolate as an intermediate the heterocyclic derivative of formula:

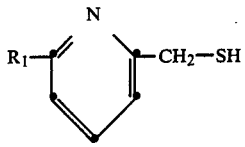
(X)

which originates from the alkaline hydrolysis of the isothiourea of formula (VIII), and then to react with it the compound of formula (IX) in the presence of an alkali metal hydroxide such as sodium hydroxide.

The isothioureas of formula (VIII), in the form of salts such as hydrochlorides, can be obtained by the action of thiourea on a derivative of formula:

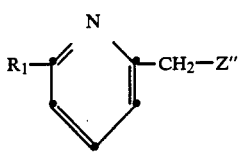
(XI)

in which Z" denotes a halogen atom, preferably a chlorine or bromine atom, optionally in the form of a salt such as a hydrohalide, working in an organic solvent such as an alcohol (ethanol) at the reflux temperature of the reaction mixture.

The derivatives of formula (XI) can be prepared by the method of W. MATHES and H. SCHÜLY, Angew. Chem. Intern. Ed. 2, 144 (1963).

(b) The compounds of formula (IV) in which X denotes sulphur or oxygen and Y denotes sulphur or oxygen can be prepared by the action of a derivative of formula:

H-X-(CH₂)₃-Y-H          (XII)

in which X and Y each denote sulphur or oxygen, on an aldehyde of formula:

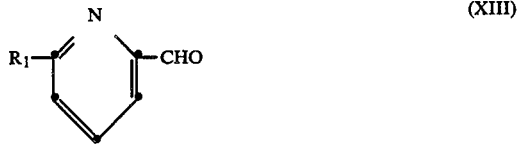
(XIII)

in which R₁ is as defined above, in a solvent which makes it possible to remove, by azeotropic distillation, the water formed during the reaction. In practice, benzene, toluene, xylenes or 1,2-dichloroethane is preferably used as the solvent.

(c) The compounds of formula (IV) in which X denotes oxygen and Y denotes a valency bond or a methylene radical can be prepared by cyclisation of a compound of formula:

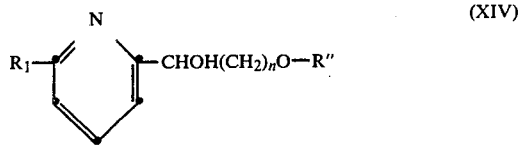
(XIV)

in which R" is a radical which protects the alcohol function, such as a tert-butyl, tert-pentyl or tetrahydropyranyl radical, n is 3 or 4 and R₁ is as defined above. The reaction is generally performed by heating this compound to reflux in a solvent such as toluene in the presence of para-toluenesulphonic acid. This treatment can optionally be followed by heating in polyphosphoric acid at a temperature between 50° and 120° C.

The compounds of formula (XIV) can be prepared by the action of a magnesium derivative of formula:

Z'''Mg-(CH₂)ₙO-R"          (XV)

in which R" and n are as defined above and Z''' denotes a halogen atom such as a bromine or iodine atom, on an aldehyde of general formula (XIII), using a method similar to that described by W. B. RENFROW., J. Org. Chem. 26, 935 (1961).

(d) The compounds of formula (IV) in which X denotes oxygen and Y denotes a valency bond or a methylene radical can also be prepared by cyclisation of a compound of formula:

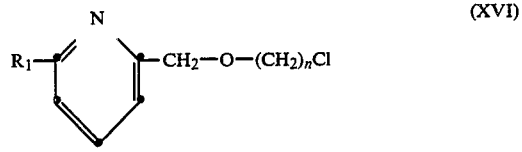
(XVI)

in which n is 3 or 4 and R₁ is as defined above.

The cyclisation is generally effected with an organic base such as an organometallic derivative, e.g. butyllithium, in an anhydrous organic solvent such as tetrahydrofuran, hexamethylphosphorotriamide or hexane or a mixture of these solvents, at a temperature in the region of −70° C.

The compounds of formula (XVI) can be prepared by the action of thionyl chloride on a compound of formula:

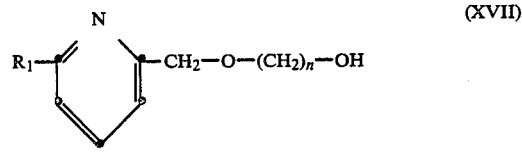
(XVII)

in which n is 3 or 4 and R₁ is as defined above, using methods known to those skilled in the art.

The compounds of formula (XVII) can be obtained by acid hydrolysis of the corresponding tetrahydropyranyl compound of formula:

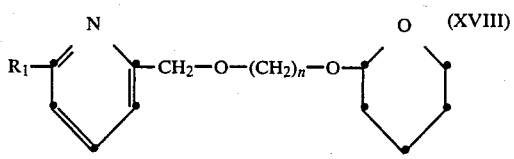

(XVIII)

in which n is 3 or 4 and $R_1$ is as defined above, using methods known to those skilled in the art.

The compounds of formula (XVIII) can be prepared by the reaction of a compound of formula:

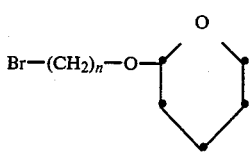

(XIX)

in which n is 3 or 4, with a compound of formula:

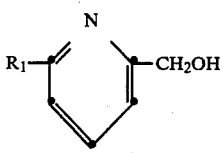

(XX)

in which $R_1$ is as defined above, using methods known to those skilled in the art.

According to a feature of the invention, the compounds of formula (I) in which $R_1$, X and Y are as defined above and R denotes a straight-chain or branched alkyl radical of 1 to 4 carbon atoms, are also obtained by the reaction of a base with a compound of formula (IV), followed by reaction of the product with an isothiocyanate of formula:

$$R'''-N=C=S \quad (XXI)$$

in which R''' denotes a straight-chain or branched alkyl radical of 1 to 4 carbon atoms.

The bases which are especially suitable for this reaction are the lithium alkyls, such as butyllithium and isopropyllithium, and phenyllithium, in solution in an inert solvent such as hexane, and metal amides such as sodium amide, lithium diethylamide or lithium diisopropylamide.

When the compound of formula (IV) is produced as described above in paragraph (a) from a compound of formula (VII) and provided the cyclisation has not been performed with an alcoholate, it is not necessary to isolate the product of formula (IV) before reacting the isothiocyanate of formula (XXI) with it. It is then only necessary to use two equivalents of the organic base.

The reaction is generally performed in an anhydrous organic solvent such as hexamethylphosphorotriamide, to which an ether such as tetrahydrofuran is generally added, at a temperature between −80° and −40° C.

When in the compound of formula (IV) X denotes a sulphur atom and Y denotes a methylene radical, it is generally more advantageous to react the isothiocyanate of general formula (XXI) with the corresponding sulphoxide, i.e. a compound of formula:

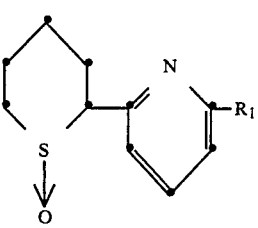

(XXII)

in which $R_1$ is as defined above, and then to reduce the sulphoxide of the product obtained so as to produce the desired compound of formula (I).

The reaction is performed in the presence of a base under the same conditions as those described above for the reaction of the isothiocyanate of formula (XXI) with the compound of formula (IV), and the reduction of the sulphoxide can be performed by any method known per se for reducing a sulphoxide to sulphide without affecting the remainder of the molecule. In particular, it is advantageous to use phosphorous pentasulphide in a chlorinated solvent such as methylene chloride, at a temperature in the region of 25° C.

The compounds of the invention can be purified by the customary physical methods, in particular crystallisation and chromatography.

The compounds of the invention exhibit an antisecretory action. This can be demonstrated in rats, using oral doses generally between 1 and 100 mg/kg, using in particular the technique of ROSSI et al., C. R. Soc. Biol., 150, 2124 (1956) or that of SHAY et al., Gastroenterology, 5, 43 (1945). The letal dose ($LD_{50}$) of the compounds of formula I in mice is generally greater than 900 mg/kg orally.

Thioformamides possessing antisecretory properties are known from the European Patent Application published under No. 0,046,417 and French Patent Application No. 79/08,032.

As compared with compounds of the prior art the compounds of the invention possess the advantage of being longer-lasting in action and/or lower toxicity.

Of special value are the compounds of formula (I) which R and $R_1$ denote a methyl radical, X denotes sulphur and Y denotes sulphur or methylene, and more particularly the product of formula (I) in which R and $R_1$ denote a methyl radical, and X and Y denote a sulphur atom.

The examples which follow illustrate the invention.

EXAMPLE 1

To a suspension of methyl 2-(6-methyl-2-pyridyl)-1,3-dithiane-2-carbodithioate (130.5 g) in 1.2 liters of ethanol maintained at a temperature in the region of 20° C., a 33% (weight/volume) solution (840 cc) of methylamine in ethanol is added dropwise in the course of 10 minutes. The mixture is then stirred for 4 hours at the same temperature. The crystals which appear are separated by filtration, washed twice with ethyl acetate (100 cc in total), 4 times with isopropyl ether (400 cc in total) and dried under reduced pressure (0.2 mm Hg; 0.03 kPa) at a temperature in the region of 20° C. The product thereby obtained (100.2 g), to which is added some product (18.4 g) prepared under the same conditions in a previous operation, is dissolved in boiling ethyl acetate (3.3 liters); to this solution is added decolorising charcoal (33 g), and the solution is filtered hot. The filter is washed 4 times with boiling ethyl acetate (400 cc in total). The filtrate and the washing liquors are combined and cooled for 4 hours to a temperature in the region of 0° C. The crystals which appear are separated by filtration, washed 4 times with ethyl acetate (200 cc in total, 6 times with isopropyl ether (600 cc in total), and then dried under reduced pressure (0.2 mm Hg; 0.03 kPa) at 55° C. N-Methyl-2-(6-methyl-2-pyridyl)-1,3-dithiane-2-carbothiamide (99.1 g), m.p. 168° C., is thereby obtained.

Methyl 2-(6-methyl-2-pyridyl)-1,3-dithiane-2-carbodithioate can be prepared in the following manner:

To a 1.6M solution (440 cc) of n-butyllithium in hexane, maintained under an atmosphere of argon and cooled to −71° C., a mixture (440 cc) of anhydrous hexamethylphosphorotriamide and anhydrous tetrahydrofuran (47:53 by volume) is added dropwise in the course of 20 minutes. A solution of 2-(6-methyl-2-pyridyl)-1,3-dithiane (97 g) in a mixture (300 cc) of anhydrous hexamethylphosphorotriamide and anhydrous tetrahydrofuran (47:53 by volume) is then added in the course of 30 minutes at a temperature in the region of −70° C. After 1 hour 40 minutes' stirring, carbon disulphide (53 g) dissolved in anhydrous tetrahydrofuran (220 cc) is added in the course of 40 minutes. After 45 minutes' stirring at −70° C., methyl iodide (97 g) dissolved in anhydrous tetrahydrofuran (220 cc) is added in the course of 30 minutes and at the same temperature. The reaction mixture is then stirred for 30 minutes at a temperature in the region of −65° C. and then for 50 minutes while the temperature is allowed to rise gradually to 10° C.; it is then poured into a mixture of distilled water (600 cc) and ethyl acetate (500 cc). After decantation, the aqueous phase is extracted twice with ethyl acetate (600 cc in total). The organic extracts are combined, washed twice with saturated aqueous sodium chloride solution (600 cc in total), anhydrous magnesium sulphate and decolorising charcoal are added, and the mixture is then kept for 15 hours at a temperature in the region of 5° C., filtered and then concentrated under reduced pressure (25 mm Hg; 3.25 kPa) at 50° C. To the product obtained (192.2 g) there is added some product (231.7 g) prepared under the same conditions in a previous operation, and the combined product is chromatographed on neutral silica gel (1.5 kg; 0.063–0.200 mm) contained in a column 8 cm in diameter. The product is eluted with methylene chloride, collecting one fraction (3.5 liters) followed by 7 fractions (600 cc). Fractions 5 to 8 are combined and concentrated to dryness under reduced pressure (25 mm Hg; 3.25 kPa) at 50° C. The product obtained (276.5 g) is dissolved in boiling ethyl acetate (200 cc). The solution obtained is cooled and kept for 1 hour at a temperature in the region of 5° C. The crystals which appear are separated by filtration, washed twice with ethyl acetate (60 cc in total) and then 3 times with isopropyl ether (135 cc in total), and dried under reduced pressure (0.2 mm Hg; 0.03 kPa) at 20° C. Methyl 2-(6-methyl-2-pyridyl)-1,3-dithiane-2-carbodithioate (153.9 g), m.p. 92° C., is thereby obtained.

2-(6-Methyl-2-pyridyl)-1,3-dithiane can be prepared in the following manner:

A solution of 6-methyl-2-pyridinecarboxaldehyde (100 g), 1,3-propanedithiol (285 g) and para-toluenesulphonic acid (11.8 g) in toluene (2.6 liters) is heated to boiling for 12 hours 40 minutes, the water formed being removed by azeotropic distillation. After being cooled to a temperature in the region of 20° C., the reaction mixture is poured into a mixture of distilled water (1 liter) and ice (500 g), and approximately 10N aqueous potassium hydroxide solution is then added dropwise. After decantation, the organic solution is washed with approximately 5N aqueous potassium hydroxide solution, and 3 times with distilled water (1700 cc in total), dried over anhydrous magnesium sulphate and concentrated to dryness under reduced pressure (25 mm Hg; 3.25 kPa) at 50° C. The product obtained (160.2 g) is chromatographed on neutral silica gel (980 g; 0.063–0.200 mm) contained in a column 8 cm in diameter. The product is eluted with a mixture of cyclohexane and ethyl acetate (70:30 by volume), collecting 300-cc fractions. Fractions 9 to 23 are combined and concentrated to dryness under reduced pressure (25 mm Hg; 3.25 kPa) at 50° C. 2-(6-Methyl-2-pyridyl)-1,3-dithiane (90.2 g), m.p. 74° C., is thereby obtained.

EXAMPLE 2

To a solution of N-methyl-2-(6-methyl-2-pyridyl)-2-tetrahydrothiopyrancarbothioamide 1-oxide (72.4 g) in methylene chloride (1.4 liters), phosphorus pentasulphide (28.5 g) is added at a temperature below 28° C. and in the course of 50 minutes. The reaction mixture is stirred for 1 hour 45 minutes at a temperature in the region of 25° C. and distilled water (250 cc) is then added. The organic phase is decanted and washed 3 times with distilled water (750 cc in total) and dried over anhydrous magnesium sulphate, decolorising charcoal is added and the mixture is kept for 15 hours at a temperature in the region of 5° C. After filtration, the solution is poured onto neutral silica gel (1.6 kg; 0.063–0.200 mm) contained in a column 8 cm in diameter. The column is eluted with methylene chloride, collecting one fraction (3.9 liters) and 13 fractions (900 cc). The column is then eluted with a mixture of cyclohexane and ethyl acetate (60:40 by volume), collecting 5 fractions (900 cc). Fractions 6 to 13 and 15 to 18 are combined and concentrated to dryness under reduced pressure (0.5 mm Hg; 0.06 kPa) at 45° C. To the product obtained (49.6 g) there is added some product (41.2 g) prepared under the same conditions in a previous operation, and the combined product is dissolved in boiling ethyl acetate (600 cc); decolorising charcoal (10 g) is added to the solution, which is filtered hot and then kept, after being cooled, for 4 hours at 0° C. The crystals which appear are separated by filtration, washed twice with ethyl acetate (30 cc in total) and 4 times with isopropyl ether (160 cc in total), and then dried under reduced pressure (0.2 mm Hg; 0.026 kPa) at 55° C. N-Methyl-2-(6-methyl-2-pyridyl)-2-tetrahydrothiopyrancarbothioamide (68.1 g), m.p. 139° C., is thereby obtained.

N-Methyl-2-(6-methyl-2-pyridyl)-2-tetrahydrothiopyrancarbothioamide 1-oxide can be prepared in the following manner:

To a solution of ferric nitrate (1.2 g) in liquid ammonia (700 cc) maintained boiling, sodium (23 g) is added in the course of 1 hour 5 minutes. After 25 minutes' stirring, a solution of 2-(6-methyl-2-pyridyl)tetrahydrothiopyran 1-oxide (106 g) in anhydrous tetrahydrofuran (500 cc) is added dropwise in the course of 40 minutes. The reaction mixture is stirred for 15 minutes; a solution of methyl isothiocyanate (74.7 g) in anhydrous tetrahydrofuran (400 cc) is then added dropwise in the course of 25 minutes. The reaction mixture is stirred for 30 minutes and is then cooled to −40° C. Ammonium chloride (70 g in total) is then added in 3 portions and stirring is then maintained for 15 hours so as to evaporate the ammonia, the temperature being allowed to rise gradually to about 20° C. Distilled water (600 cc) and ethyl acetate (650 cc) are then added to the mixture. After 15 minutes' stirring, the crystals which appear are separated by filtration, washed 3 times with ethyl acetate (180 cc in total) and 6 times with isopropyl ether (900 cc in total), and then dried under reduced pressure (0.3 mm Hg; 0.04 kPa) at a temperature in the region of 20° C. A first batch (45 g) of N-methyl-2-(6-methyl-2-pyridyl)-2-tetrahydrothiopyrancarbothioamide 1-oxide, m.p. 234° C., is thereby obtained. After decantation of the filtrate, the organic phase and the ethyl acetate washing liquors are combined, washed 3 times with distilled water (1500 cc), and dried over anhydrous magnesium sulphate, decolorising charcoal is added and the mixture is filtered and concentrated to dryness under reduced pressure (25 mm Hg; 3.25 kPa). The product obtained (125 g) is dissolved in ethyl acetate (400 cc) and then kept for 15 hours at a temperature in the region of 5° C. The crystals which appear are separated by filtration, washed twice with ethyl acetate (60 cc in total) and 5 times with isopropyl ether (300 cc in total) and dried under reduced pressure (0.2 mm Hg; 0.026 kPa) at a temperature in the region of 20° C. A second batch (17.8 g) of N-methyl-2-(6-methyl-2-pyridyl)-2-tetrahydrothiopyrancarbothioamide 1-oxide, m.p. 234° C., is thereby obtained.

2-(6-Methyl-2-pyridyl)tetrahydrothiopyran 1-oxide can be prepared in the following manner:

To a solution of potassium tert-butylate (128 g) in anhydrous tetrahydrofuran (800 cc) maintained at a temperature below 15° C. under an atmosphere of argon, a solution of 2-[(4-chlorobutyl)sulphinylmethyl]-6-methylpyridine (176.7 g) in anhydrous tetrahydrofuran (560 cc) is added dropwise in the course of 1 hour, and the reaction mixture is stirred for 2 hours at a temperature in the region of 20° C. Distilled water (1000 cc) and methylene chloride (800 cc) are then added to the mixture, which is then filtered. The aqueous phase is decanted and saturated by adding sodium chloride, methylene chloride (800 cc) is added and the mixture is filtered and decanted. The organic phases are combined, dried over anhydrous magnesium sulphate and concentrated under reduced pressure (20 mm Hg; 2.7 kPa) at 40° C. A first batch (109.8 g of product is thereby obtained. The aqueous phase is again extracted with methylene chloride (600 cc). The organic phase is decanted, dried over anhydrous magnesium sulphate and concentrated to dryness under reduced pressure (20 mm Hg; 2.7 kPa) at 35° C. The product thereby obtained (20.2 g) is added to some product (102 g) originating from the first batch, and the mixture is chromatographed on neutral silica gel (1,350 g; 0.063–0.200 mm) contained in a column 8.5 cm in diameter. The column is eluted with ethyl acetate (3.4 liters), collecting one fraction (2,200 cc) and 4 fractions (300 cc), and with a mixture (9,600 cc) of ethyl acetate and methanol (90:10 by volume), collecting 32 fractions (300 cc). Fractions 6 to 37 are combined and concentrated to dryness under reduced pressure (20 mm Hg; 2.7 kPa) at 50° C. 2-(6-Methyl-2-pyridyl)tetrahydrothiopyran 1-oxide (90 g), m.p. 100° C., is thereby obtained.

2-[(4-Chlorobutyl)sulphinylmethyl]-6-methylpyridine can be prepared in the following manner:

To a solution of 4-chlorobutyl(6-methyl-2-pyridyl)methyl sulphide (9.2 g) in methylene chloride (140 cc), an 82.5% strength solution of meta-chloroperbenzoic acid (8.2 g) in methylene chloride (90 cc) is added dropwise in the course of 1 hour 30 minutes at a temperature in the region of 15° C. The mixture is stirred for 16 hours at a temperature in the region of 20° C. and then poured into neutral silica gel (225 g; 0.063–0.200 mm) contained in a column 4.3 cm in diameter. The column is eluted successively with methylene chloride (2.5 liters), a mixture (500 cc) of methylene chloride and ethyl acetate (50:50 by volume), ethyl acetate (500 cc) and a mixture (1.25 liters) of ethyl acetate and methanol (90:10 by volume), collecting 250-cc fractions. Fractions 15 to 19 are combined and concentrated to dryness under reduced pressure (20 mm Hg; 2.7 kPa) at 50° C. 2-[(4-Chlorobutyl)sulphinylmethyl]-6-methylpyridine (8.8 g) is thereby obtained in the form of a yellow oil, and this is used without further purification in the subsequent syntheses.

4-Chlorobutyl(6-methyl-2-pyridyl)methyl sulphide can be obtained according to the method described in European Patent Application No. 0,046,417 for 4-chlorobutyl 2-pyridylmethyl sulphide. A colourless, mobile oil is thereby obtained; Rf equals 0.53 (thin layer chromatography on silica gel; solvent, cyclohexane/ethyl acetate 70:30).

EXAMPLE 3

To a 1.6M solution (3,150 cc) of n-butyllithium in hexane maintained under an atmosphere of nitrogen at between −65° and −70° C., a mixture (1,680 cc) of anhydrous tetrahydrofuran and anhydrous hexamethylphosphorotriamide (50:50 by volume) is added slowly, followed by a solution of 3-chloropropyl(6-methyl-2-pyridyl)methyl ether (360 g) in a mixture (1,080 cc) of anhydrous tetrahydrofuran and anhydrous hexamethylphosphorotriamide (50:50 by volume) added dropwise in the course of 1 hour. After 5 minutes' stirring, a solution of methyl isothiocyanate (158 g) in a mixture (432 cc) of anhydrous tetrahydrofuran and anhydrous hexamethylphosphorotriamide (50:50 by volume) is added in the course of 35 minutes. The mixture is stirred for 1 hour at −60° C. and distilled water (4,800 cc) is then added slowly, the temperature being allowed to rise to about 20° C. The mixture is stirred for 5 minutes and then extracted with ethyl acetate (2,400 cc). The aqueous phase is decanted and extracted 4 times with ethyl acetate (6,000 cc in total). The organic liquors are combined, washed twice with aqueous sodium chloride solution (1,800 cc in total) at a concentration of 180 g per liter, and then extracted 3 times with 2N aqueous hydrochloric acid solution (4,500 cc in total). The acidic aqueous extracts are combined, washed twice with diethyl ether (3,000 cc in total) and then brought to a pH in the region of 8 using 10N aqueous sodium hydroxide solution. The mixture is extracted 4 times with ethyl acetate (10 liters in total). The organic extracts are combined, washed twice with distilled water (3.6 liters in total), dried over anhydrous magnesium sulphate in the presence of decolorising charcoal (18 g) for 1 hour and then filtered. The filtrate is concentrated to a small volume under reduced pressure (30 mm Hg; 4 kPa) at a temperature in the region of 35° C. The crystallised product is separated by filtration, washed with isopropanol (180 cc) and dried in a stream of air. The product obtained (118 g) is dissolved in boiling absolute ethanol (472 cc). To the solution is added decolorising charcoal (1 g), and the mixture is filtered hot. The filter is washed with a little boiling ethanol, and the solution is then cooled in an ice bath for 1 hour. The crystals which appear are separated by filtration, washed with ice-cooled absolute ethanol (120 cc) and dried in a stream of air at 20° C. N-Methyl-2-(6-methyl-2-pyridyl)-2-tetrahydrofurancarbothioamide (110 g), m.p. 151.4° C., is thereby obtained.

3-Chloropropyl(6-methyl-2-pyridyl)methyl ether can be prepared in the following manner:

To a solution of sulphinyl chloride (260 g) in chloroform (450 cc) maintained at a temperature below 10° C., 3-hydroxypropyl(6-methyl-2-pyridyl)methyl ether (339 g) is added in the course of 30 minutes. The mixture is then heated gradually and then maintained boiling for 1 hour. After being cooled to about 20° C., the mixture is concentrated under reduced pressure (30 mm Hg; 4 kPa) at 50° C. The product obtained is dissolved in distilled water (1,000 cc) and the solution obtained is washed 3 times with diethyl ether (1,035 cc in total), filtered and then neutralised in the presence of diethyl ether (670 cc) with sodium bicarbonate (160 g). The decanted aqueous phase is saturated with sodium chloride and then extracted 3 times with diethyl ether (600 cc in total). The extracts are combined, dried over anhydrous magnesium sulphate in the presence of decolorising charcoal (17 g) and filtered. The filtrate is concentrated to dryness under reduced pressure (30 mm Hg; 4 kPa). 3-Chloropropyl(6-methyl-2-pyridyl)methyl ether (359.4 g) is thereby obtained in the from of a brown oil, and this is used as it is in the subsequent syntheses.

3-Hydroxypropyl(6-methyl-2-pyridyl)methyl ether can be prepared in the following manner:

To (6-methyl-2-pyridyl)methyl 3-(2-tetrahydropyranyloxy)propyl ether (888 g) cooled to about 10° C., N aqueous hydrochloric acid solution (3,700 cc) is added while the temperature is maintained at about 10° C., the temperature is then allowed to rise to about 20° C. and the mixture is stirred for 16 hours. The mixture is extracted 3 times with ethyl acetate (2,400 cc in total) and the reaction mixture is then neutralised with 10N aqueous sodium hydroxide solution (370 cc). The mixture is extracted 4 times with ethyl acetate (3,100 cc in total). The organic extracts are combined and washed 5 times with distilled water (2,500 cc in total), then dried over anhydrous magnesium sulphate and filtered. The filtrate is concentrated to dryness under reduced pressure (300 mm Hg; 4 kPa). The oil obtained is distilled under reduced pressure (0.8 mm Hg; 0.11 kPa), collecting the products which distil over at a temperature below 140° C. The latter are redistilled under reduced pressure (0.25 mm Hg; 0.03 kPa) with a column 4 cm in diameter and 18 cm high equipped with 7-mm Raschig rings. 3-Hydroxypropyl(6-methyl-2-pyridyl)methyl ether (371 g), which distils at 104°-108° C. under 0.25 mm Hg (0.03 kPa), is thereby obtained.

(6-Methyl-2-pyridyl)methyl 3-(2-tetrahydropropyranyloxy)propyl ether can be prepared in the following manner:

To a suspension of potassium carbonate (338 g) tetrabutylammonium hydrogensulphate (52 g) and powdered potassium hydroxide (323 g) in a mixture of tetrahydrofuran (602 cc) and 2-hydroxymethyl-6-methylpyridine (301 g), 1-bromo-3-(2-tetrahydropyranyloxy)-propane (737 g) is added at a temperature below 50° C. and with brisk stirring. The temperature is then allowed to rise to about 20° C. and the mixture is stirred for 16 hours. Distilled water (2,000 cc) and diethyl ether (500 cc) are then added to the reaction mixture, which is then decanted. The organic extract is washed 5 times with distilled water (1,750 cc in total). The aqueous phases are combined and extracted 3 times with diethyl ether (1,035 cc) in total. The organic extracts are combined, dried over anhydrous magnesium sulphate in the presence of decolorising charcoal (15 g) and filtered. The filtrate is concentrated under reduced pressure (30 mm Hg; 4 kPa) at 50° C. (6-Methyl-2-pyridyl)methyl 3-(2-tetrahydropyranyloxy)propyl ether (683 g) is thereby obtained in the form of an oil. (Rf=0.50, thin layer chromatography on silica; solvent: ethyl acetate).

The present invention also provides pharmaceutical compositions comprising a thioformamide of formula (I), in combination with one or more compatible pharmaceutically acceptable diluents or adjuvants, which can be inert or physiologically active. The compositions of the invention can be used orally, parenterally or rectally.

As solid compositions for oral administration, tablets, pills, powders (especially in gelatin capsules or wafer capsules) or granules can be used. In these compositions, the active product according to the invention is mixed with one or more inert diluents such as starch, cellulose, sucrose, lactose or silica. These compositions can also contain substances other than diluents, for example one or more lubricants such as magnesium stearate or talc, a colouring, a coating (dragées) or a lacquer.

As liquid compositions for oral administration, there can be used pharmaceutically acceptable solutions, suspensions, emulsions, syrups and elixirs containing inert diluents such as water, ethanol, glycerol, vegetable oils or liquid paraffin. These compositions can also contain substances other than the diluents, for example wetting, sweetening, thickening, flavouring or stabilising products.

Sterile compositions for parenteral administration can preferably be aqueous or non-aqueous solutions, suspensions or emulsions. As solvent or vehicle, there can be used water, propylene glycol, polyethylene glycol, vegetable oils especially olive oil, injectable organic esters, e.g. ethyl oleate, or other suitable organic solvents. These compositions can also contain adjuvants, especially wetting agents, agents for achieving isotonicity, emulsifiers, dispersants and stabilisers. The sterilisation can be accomplished in several ways, e.g. by asepticising filtration, by incorporating sterilising agents in the composition, by irradiation or by heating. The compositions can also be prepared in the form of sterile solid compositions which can be dissolved at the time of use in an injectable sterile medium.

Compositions for rectal administration are suppositories or rectal capsules which contain, in addition to the active product, excipients such as cocoa butter, semisynthetic glycerides or polyethylene glycols.

The thioformamides of the invention reduce gastric secretion and are therefore useful in human therapy in the treatment of gastrointestinal ulcers. The dosage depends on the condition of the patient, the effect sought and the period of treatment. It is generally between 25 and 1,000 mg per day orally for an adult, in one or more doses. In geneal, the doctor will determine the posology which he judges to be the most suitable in accordance with the age and weight and all the other factors appropriate to the subject to be treated.

The Example which follows illustrates a composition according to the invention.

EXAMPLE A

Tablets containing 50-mg doses of active product and having the following composition are prepared according to the customary technique:

| | |
|---|---|
| N—methyl-2-(6-methyl-2-pyridyl)-1,3-dithiane-2-carbothioamide | 50 mg |
| starch | 60 mg |
| lactose | 50 mg |
| magnesium stearate | 2 mg |

We claim:

1. N-Methyl-2-(6-methyl-2-pyridyl)-1,3-dithiane-2-carbothiamide.

2. A pharmaceutical composition useful for inhibiting gastric secretion comprising an effective amount of a thioformamide according to claim 1, in combination with one or more compatible and pharmaceutically acceptable diluents or adjuvants.

3. Method of inhibiting gastric secretion which comprises administering to a subject in whom such inhibition is desired an effective amount of a thioformamide as claimed in claim 1.

* * * * *